(12) United States Patent
Sudo et al.

(10) Patent No.: US 6,924,105 B2
(45) Date of Patent: Aug. 2, 2005

(54) METHOD OF ANALYZING DOUBLE STRANDED DNA

(75) Inventors: Yukio Sudo, Saitama (JP); Yoshihiko Makino, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 48 days.

(21) Appl. No.: 10/039,642

(22) Filed: Oct. 24, 2001

(65) Prior Publication Data

US 2002/0177146 A1 Nov. 28, 2002

(30) Foreign Application Priority Data

Oct. 25, 2000 (JP) .......................... 2000-325136
Oct. 31, 2000 (JP) .......................... 2000-332249

(51) Int. Cl.[7] .......................... C12Q 1/68; G01N 33/53; C12P 19/34; A61K 39/395; A61K 38/00
(52) U.S. Cl. .......................... 435/6; 435/7.1; 435/91.1; 424/130.1; 530/300; 530/350; 536/23.1; 536/24.3; 536/24.33; 204/450
(58) Field of Search .......................... 435/6, 7.1, 91.1, 435/183; 436/94, 501; 536/23.1, 24.3, 24.33, 25.3; 204/450; 424/130.1; 530/300, 350

(56) References Cited

U.S. PATENT DOCUMENTS 4,623,627 A   11/1986   Huang et al. ................ 435/240
4,868,111 A * 9/1989   Bujard et al. ................ 435/68
5,789,167 A   8/1998   Konrad ........................ 435/6
5,912,129 A * 6/1999   Vinayagamoorthy et al. .. 435/6

FOREIGN PATENT DOCUMENTS

EP       0478319 A1    4/1992
WO       WO 00/05408   2/2000

OTHER PUBLICATIONS

Piunno et al., Fiber–optic DNA sensor for fluorometric nucleic acid determination. Anal. Chem., 67, 2635–2643, 1995.*

Liu et al., voltammetric determination of sequence–specific DNA by electroactive intercalator on graphite electrode. Analytica Chimica Acat, 335, 239–243, 1996.*

* cited by examiner

Primary Examiner—Kenneth R. Horlick
Assistant Examiner—Frank W Lu
(74) Attorney, Agent, or Firm—Reed Smith LLP

(57) ABSTRACT

The object of the present invention is to provide a method for analyzing double stranded DNA directly without denaturation. According to the present invention, there is provided a method of analyzing double stranded DNA present in an analyte, which comprises the steps of:

(1) contacting the analyte with a double stranded DNA recognizing substance immobilized on a support, and
(2) measuring double stranded DNA bound to the double stranded DNA recognizing substance.

9 Claims, No Drawings

METHOD OF ANALYZING DOUBLE STRANDED DNA

CROSS-REFERENCES TO RELATED APPLICATIONS

This application claims priority of Japanese Application Nos. 325136/2000 filed Oct. 25, 2000 and 332249/2000 filed Oct. 31, 2000, the complete disclosure of which is hereby incorporated by reference.

FIELD OF THE INVENTION

The present invention relates to a method of analyzing a double stranded nucleic acid (especially, double stranded DNA) present in an analyte and also relates to a method of quantifying an amount of double stranded nucleic acid present in an analyte. Further, where the present invention is applied to gene analysis, it can be used in analysis and mapping of gene polymorphisms such as SNPs (Single Nucleotide Polymorphisms) etc. Further, the present invention can also be employed to detect an exogenous gene group derived from a virus or bacteria present in an analyte.

BACKGROUND OF THE INVENTION

A method which involves immobilizing either one of a targeted nucleic acid sample or a nucleic acid probe which is a DNA or RNA fragment comprising a nucleotide sequence complementary to a targeted nucleic acid sample, and performing hybridization between them, was developed in 1975 by E. M. Southern. This method has come to be widely used as Southern blotting (J. Mol. Biol 98, 503 (1975)). In Southern blotting, a nucleic acid sample is electrophoresed and thereafter immobilized on a nitrocellulose or nylon membrane or the like, then contacted with a nucleic acid probe having a complementary sequence.

In contrast to the above method, a method which involves immobilizing a nucleic acid probe and contacting it with a target nucleic acid to measure an amount of target nucleic acid, has also been developed and is used in gene mapping, genetic diagnosis and the like. Further, Southern et al have developed a DNA array where multiple nucleic acid probes are immobilized on a support in an array form, and have showed that DNA on a glass support binds to the complementary DNA. Further, Affymax Inc. has succeeded in developing a high densification technique of DNA array by combining Southern's technique with a DNA solid-phase synthesis technique using a photoresist method, and has commercialized this in the form of GeneChip (S. Fodor; Science 277, 393 (1997), Nature Genetics Supplement 21, 20 (1999)).

In this way, methods of detecting DNA using hybridization have been greatly advanced. However, the above mentioned methods of analysis, while being extremely effective in the detection of single stranded nucleic acid such as mRNA, when applied to the detection of double stranded nucleic acids, require a complex operation of heat-denaturing the double stranded nucleic acid present in an analyte for converting it into single strands prior to hybridization.

For example, where the subject of analysis is DNA in a genome, the subject DNA forms a double strand. For example, detection of SNP has been conducted by P. N. Gillies et al. with electric address method (Nature Biotechnology, 17, 365 (1999)) and further by R. J. Cho et al. with high-density oligo-DNA array (Nature Genetics 23, 203 (1999)). However, in either case, the determination of DNA involves a complex operation including denaturation into a single strand by heat denaturation after amplification by PCR of a target DNA portion present in a sample.

As a method for detecting double stranded DNA, use of an intercalator is known. In Japanese Patent No. 2573443, there is disclosed a method of detecting DNA using an intercalator. However, even with this method, in order to allow reaction with immobilized DNA, there is a need to firstly denature double stranded DNA into single strands.

SUMMARY OF THE INVENTION

The object of the present invention is to solve the problems in the above conventional techniques. That is, an object of the present invention is to provide a method for analyzing a double stranded DNA directly without denaturation. A further object of the present invention is to provide a simple and high-sensitive method of analyzing double stranded DNA. Further, another object of the present invention is to provide a method of analyzing double stranded DNA which enables a quick and high sensitive detection of a gene and polymorphism thereof.

A still further object of the present invention is to provide a method for promoting reaction speed in a method for analyzing a double stranded DNA directly without denaturation. A still further object of the present invention is to provide a method of increasing signal/noise ratio by removing non-specifically adsorbent double stranded DNA which is transported into the vicinity of a double stranded recognizing substance. A still further object of the present invention is to provide a method for increasing precision of analysis of SNPs and the like by remove the double stranded DNA which binds weakly with the double stranded DNA recognizing substance from the double stranded DNA recognizing substance.

As a result of diligent studies directed toward the above objects, the present inventors have found that it is possible to analyze a double stranded DNA directly without denaturation by contacting an analyte with a double stranded DNA recognizing substance immobilized on a support, and measuring an amount of double stranded DNA bound to the double stranded DNA recognizing substance. Further, the present inventors found that it is possible to detect, with high sensitivity, an amount of double stranded DNA bound to a double stranded DNA recognizing substance by using a double strand insertion agent such as a DNA intercalator.

Further, the present inventors have found that it is possible to analyze a double stranded DNA directly without denaturation of the double stranded DNA at an improved reaction speed, by contacting an analyte with a double stranded DNA recognizing substance immobilized on a support, promoting binding between the double stranded DNA recognizing substance immobilized on the support and the double stranded DNA in the analyte by applying an electric field between the support on which the double stranded DNA recognizing substance is immobilized and a solution containing the analyte and thereafter measuring double stranded DNA bound to the double stranded DNA recognizing substance.

Further, the present inventors have found that it is possible to increase signal/noise ratio by applying an electric field between a support on which the double stranded DNA recognizing substance is immobilized and the analyte to promote binding between the double stranded DNA recognizing substance immobilized on the support and the double stranded DNA present in the analyte, and thereafter applying an electric field in a direction which is opposite to the direction of the above electric field to remove non-specific adsorbed DNA and DNA that binds weakly to the double stranded DNA recognizing substance.

The present invention was completed on the basis of these findings.

According to the present invention, there is provided a method of analyzing double stranded DNA present in an analyte, which comprises the steps of:
(1) contacting the analyte with a double stranded DNA recognizing substance immobilized on a support, and
(2) measuring double stranded DNA bound to the double stranded DNA recognizing substance.

In another embodiment of the present invention, there is provided a method of analyzing double stranded DNA present in an analyte, which comprises the steps of:
(1) contacting the analyte with a double stranded DNA recognizing substance immobilized on a support,
(2) applying an electric field between the support on which the double stranded DNA recognizing substance is immobilized and the analyte, to direct double stranded DNA present in an analyte toward the double stranded DNA recognizing substance immobilized on the support, and
(3) measuring double stranded DNA bound to the double stranded DNA recognizing substance.

In a further another embodiment of the present invention, there is provided a method of analyzing double stranded DNA present in an analyte, which comprises the steps of:
(1) contacting the analyte with a double stranded DNA recognizing substance immobilized on a support,
(2) applying an electric field between the support on which the double stranded DNA recognizing substance is immobilized and the analyte, to direct double stranded DNA present in an analyte toward the double stranded DNA recognizing substance immobilized on the support,
(3) applying an electric field in a direction which is opposite to the direction of the electric field applied in step (2), and
(4) measuring double stranded DNA bound to the double stranded DNA recognizing substance.

Preferably, the double stranded DNA recognizing substance is a double stranded DNA recognizing antibody, a DNA transcription factor, a protein having Zn finger motif or Ring Finger motif, or a peptide nucleic acid.

Preferably, in the step of measuring the double stranded DNA bound to the double stranded DNA recognizing substance, an insertion agent which recognizes double stranded DNA is added to a reaction system, and the double stranded DNA present in the analyte is measured by detecting the insertion agent inserted into the double stranded DNA.

Preferably, the insertion agent is a DNA intercalator.

Preferably, the DNA intercalator has an electrochemical activity, and the double stranded DNA present in the analyte is measured by detecting the DNA intercalator by electrochemical means.

Preferably, the DNA intercalator is detected by a fluorescence, luminescence or surface plasmon method.

DETAILED DESCRIPTION OF THE INVENTION

The embodiments of the present invention will be explained in detail below.

The method of analyzing double stranded DNA present in an analyte according to the present invention comprises the steps of:
(1) contacting the analyte with a double stranded DNA recognizing substance immobilized on a support, and
(2) measuring double stranded DNA bound to the double stranded DNA recognizing substance.

The types of "analyte" used herein are not particularly limited so long as the analyte includes double stranded DNA. For example, blood such as peripheral venous blood, leukocyte, serum, urine, feces, semen, saliva, cultured cells, tissue cells such as cells of various organs, or any other samples which comprise nucleic acid, can be used. For an analyte, samples of tissue cells and the like described above may be used as they are, and preferably cells in an analyte sample are disrupted and an analyte in which double stranded DNA has been released is used. Disruption of cells in an analyte sample can be performed by usual methods, e.g. by physical action exerted from outside such as by shaking, ultrasonification or the like. Also, nucleic acid can be released from cells by using nucleic acid extraction solution (e.g. surfactants such as SDS, Triton-X or Tween-20, or solutions containing saponins, EDTA, protease and the like). When eluting nucleic acid with a nucleic acid extraction solution, reaction can be promoted by incubating at a temperature of 37° C. or more.

In the present invention, a double stranded DNA recognizing substance immobilized on a support is used. The support used in the present invention is not particularly limited so long as the double stranded DNA recognizing substance explained below can be immobilized thereon. Examples of a preferred support include non-porous supports such as glass, quartz, plastic, an electrode and the like.

The materials for electrodes include carbon electrodes such as graphite or glassy carbon; noble metal electrodes such as platinum, gold, palladium or rhodium; oxide electrodes such as titanium oxide, tin oxide, manganese oxide or lead oxide; semiconductor electrodes such as those of Si, Ge, ZnO or CdS; and electronic conductors such as titanium. The use of gold or glassy carbon is particularly preferable. These electrical conductors may be coated with a conductive polymer or they may be covered with a monomolecular membrane.

Further, a porous support such as nitrocellulose membrane, nylon membrane or PVDF membrane may be used as a support, and a composite of a non-porous support and a porous support can also be used.

A double stranded DNA recognizing substance used in the present invention means a substance which recognizes double stranded DNA and specifically binds thereto. Specific examples of a double stranded DNA recognizing substance include DNA transcription factor, mismatch repair protein, double stranded DNA recognizing antibody, and peptide nucleic acid.

DNA transcription factor is a substance which binds to a promoter region on a gene and controls transcription from DNA to mRNA (Tamura Takaaki: Transcription Factors (Yodosha 1995)). Therefore, a transcription factor is known to specifically bind to a double stranded DNA having a specific sequence.

Among the numerous transcription factors in existence, Zinc Finger Protein, i.e. a group of transcription factors having a Zinc Finger or Ring Finger motif, has an extremely high rate of appearance in eukaryotic organisms, with apparently 1% of the genome encoding this protein. Pabo et al. analyzed the tertiary structure of Zinc Finger motif and revealed the mechanism of binding with DNA (Science, 252, 809 (1991)). Further, Choo et al have succeeded in producing, with gene recombinant techniques, a group of Zinc Finger proteins which are not present in nature, and which bind to specific sequences (Nature 372, 642 [1994], PNAS91, 11163 (1994)). Further, a group of Scripps Research Institute has succeeded in producing a novel group of Zinc Finger proteins by a Phage Display (PNAS 95, 2812, [1998]: 96, 2758 (1999)). In this way, a group of DNA transcription factors such as Zinc Finger Protein originally possess a property of binding to double stranded DNA. According to research in recent years, it is becoming possible to produce a recombinant which recognizes any DNA sequence. In this way, it is possible to efficiently capture double stranded DNA on a support by immobilizing protein.

A mismatch repair protein is an enzyme which repairs inappropriate base pairs (irregular or mismatched pairs) occurring between double strands of DNA. For example, in the case of $E.coli$ DNA polymerase, a nucleotide which does not form a pair with a base of template DNA, is incorporated at a frequency of about one site in $10^8$ base pairs. However, this is repaired by a mismatch repair enzyme. A mismatch repair enzyme binds to DNA immediately after replication within cells, and remove a portion comprising a mismatched base pair. In the present invention, by exploiting the property of a mismatch repair protein of binding to double stranded DNA, it is possible to use the protein as a double stranded DNA recognizing substance.

It is well known that antibodies which recognize double stranded DNA appear in the sera of systemic lupus erythematosus patients. It is becoming possible to produce such double stranded DNA recognizing monoclonal antibodies as a result of the development of antibody preparation techniques and gene recombination techniques (Suzuki et al, Int J Mol Med 3, 385, 1999, Barry et al, J Biol Chem 269, 3623(1994)). In this way, a double stranded DNA recognizing antibodies can be used as the double stranded DNA recognizing protein in the present invention.

In peptide nucleic acid, sugar and phosphate portions which is the skeleton structure of DNA are replaced with a polyamide skeleton. The peptide nucleic acid is known to specifically hybridize with DNA to form a double strand (P. E. Nielesen et al, Science, 254, 1497(1991); Gene and Biotechnology: N. Sugimoto, Maruzen, 1999). Although the peptide nucleic acid is functionally similar with DNA, the structure is completely different with each other. The peptide nucleic acid has a polyamide basic skeleton and contains no sugar or phosphate within its molecule. Further, the peptide nucleic acid is able to insert itself within DNA-DNA strands to form a triple strand. In the present invention, by exploiting this property, the peptide nucleic acid can be used as a double stranded DNA recognizing substance.

The above-mentioned double stranded DNA recognizing substance can be directly immobilized on a support. Concretely, a solution containing a double stranded DNA recognizing substance is spotted on a support, and allowed to stand for a certain period, thereby enabling double stranded DNA recognizing substance to be immobilized on a support.

According to a preferred embodiment, the method of analyzing a double stranded DNA present in an analyte according to the present invention, comprises the steps of:
(1) contacting the analyte with a double stranded DNA recognizing substance immobilized on a support,
(2) applying an electric field between the support on which the double stranded DNA recognizing substance is immobilized and the analyte, to direct double stranded DNA present in an analyte toward the double stranded DNA recognizing substance immobilized on the support, and
(3) measuring double stranded DNA bound to the double stranded DNA recognizing substance.

The method of applying an electric field is not particularly limited, but it is necessary to apply an electric field in such a direction that double stranded DNA present in an analyte is directed toward the double stranded DNA recognizing substance immobilized on the support. By applying such an electric field, binding between double stranded DNA recognizing substance immobilized on a support and double stranded DNA in an analyte is promoted. Double stranded DNA typically has a negative charge, and so it is possible to promote binding between double stranded DNA recognizing substance immobilized on a support and double stranded DNA in an analyte by placing an anode on the side of the support on which double stranded DNA recognizing substance is immobilized, or making the support itself the anode, and placing a cathode within the analyte containing double stranded DNA (preferably the analyte being a solution), and applying an electric field between the anode and the cathode.

It is preferred that the potential difference of an electric field for directing double stranded DNA in an analyte to the double stranded DNA recognizing substance immobilized on a support is within a range of 0 to +2V (that is, the potential of support side is 0 to +2V higher than that of the analyte fluid).

One preferred embodiment of the present invention includes a process of preparing an electrode on which a substance which binds to double stranded DNA is immobilized, contacting an analyte fluid with the electrode, and thereafter applying an electric field (difference in potential) between the electrode and the analyte fluid.

According to one preferred embodiment, the method of analyzing double stranded DNA present in an analyte according to the present invention comprises the steps of:
(1) contacting the analyte with a double stranded DNA recognizing substance immobilized on a support,
(2) applying an electric field between the support on which the double stranded DNA recognizing substance is immobilized and the analyte, to direct double stranded DNA present in an analyte toward the double stranded DNA recognizing substance immobilized on the support,
(3) applying an electric field in a direction which is opposite to the direction of the electric field applied in step (2), and
(4) measuring double stranded DNA bound to the double stranded DNA recognizing substance.

Here, step (2) can be conducted in a manner similar to the above.

Step (3) is a step of applying an electric field in a direction which is opposite to the direction of the electric field in step (2). By placing a cathode on the side of the support on which double stranded DNA recognizing substance is immobilized, or making the support itself the cathode, and placing a anode in the analyte which contains double stranded DNA (preferably the analyte being a solution), and applying an electric field between the anode and the cathode, double stranded DNA in the vicinity of the double stranded DNA recognizing substance immobilized on the support can be removed from the support. In this way, by adopting the above step (3), non-specifically adsorbed DNA, and DNA which binds weakly to the double stranded DNA recognizing substance, can be removed from the support, thereby allowing signallnoise ratio to be improved.

It is preferred that the difference in potential of the oppositely directed potential is within a range of 0 to −2V (i.e. the potential of the support side is 0 to +2V lower than that of the analyte fluid).

One preferred embodiment of the present invention includes a process of preparing an electrode on which a substance which binds to double stranded DNA is immobilized, contacting an analyte fluid with the electrode, thereafter applying potential between the electrode and the analyte fluid, and further thereafter applying potential in a direction which is opposite to the direction of the above-mentioned potential to remove unnecessary DNA molecules.

Target DNA in an analyte is preferably detected directly without amplification by PCR and the like. Detection may be performed after amplification.

The target DNA or amplified product thereof can be easily detected by labeling in advance. To label DNA, methods using enzymes (Reverse Transcriptase, DNA polymerase, RNA Polymerase, Terminal deoxytransferase- and the like) are well known. A labeling substance may be directly bound by chemical reaction. Regarding such labeling methods, known techniques are described in texts (S. Nomura, *Protocols for Experiments without Isotopes* 1, Shujunsha 1994, *Protocols for Experiments without Isotopes* 2, Shujunsha 1998; M. Muramatu, *DNA micro-array and Most Recent PCR Labeling Substances Shujunsha* 2000). It is preferred that the labeling substance is a substance which can produce a detectable signal. Where the labeling substance is a substance capable of amplifying a signal such as an enzyme or catalyst, sensitivity of DNA detection is greatly improved. The labeling substance may also be one of a specifically binding pair such as biotin-avidin, antigen-antibody or hapten-antibody, and the labeling substance may be bound to a target DNA via its binding partner.

However, since the above-described labeling procedure is generally complicated, an example of a more preferred detection method is that where DNA in an analyte is measured without labeling. For this purpose, for example, a DNA insertion agent which recognizes a double stranded DNA, so-called a DNA intercalator, can be used. By use of a DNA intercalator, not only the detection procedure is simplified, but also the detection sensitivity is increased. For example, when a DNA of 1000 bp is detected, with the so-called labeling method, at most only several labeling substances can be introduced, whereas if an intercalator is used, it is possible to introduce more than 100 labeling substances.

Double stranded DNA insertion agent (DNA intercalator) may be added after reaction between double stranded DNA which is the analyte and double stranded DNA recognizing substance on the support, or it may be added at the time of reaction.

A DNA intercalator may itself be a substance capable of forming a detectable signal. Alternatively, a signal forming substance may be bound to a side chain thereof, or bound to an intercalator by means of a specifically binding pair such as biotin-avidin, antigen-antibody or hapten-antibody.

In the present invention, detectable signals are preferably signals that can be detected by for example, fluorescence detection, luminescence detection, chemiluminescence detection, bio-luminescence detection, electrochemical luminescence detection, radioactivity detection, electrochemical detection, or calorimetric detection, but are not limited thereto.

Preferred examples of the DNA intercalator include an intercalator which itself has signal forming ability such as a fluorescent pigment, and a complex of an intercalator and a signal forming substance. Examples of a complex of an intercalator and a signal forming substance include those represented by the following formulae (1) and (2):

X—L1—I—L2—Y   Formula (1)

X—L1—I   Formula (2)

(In the formulae (1) and (2), I indicates a substance to be inserted into double stranded DNA, L1 and L2 represent linker sequences, and X and Y represent detectable molecules.)

In the formulae (1) and (2), the substance to be inserted into double stranded DNA represented by I preferably has a plate-form insertion group such as a phenyl group in its molecule, and refers to a substance which can bind to double stranded DNA by inserting the insertion group between one base pair and another base pair in double stranded DNA.

In the formulae (1) and (2), the linker sequences represented by L1 and L2 are not particularly limited, and examples thereof include an alkylene group, —O— group, —CO— group, —NH— group, and a group consisting of a combination thereof.

In the formulae (1) and (2), specific examples of the detectable molecule represented by X and Y include fluorescent pigments such as Fluorescein, Rhodamin, Cy5, Cy3, Texas Red, and ruthenium complex; substances which form specifically binding pairs such as biotin-avidin, antigen-antibody and hapten-antibody; electrochemically detectable substances such as ferrocene derivatives; luminescent substances such as lucigenin derivatives and luminol derivatives; and enzymes such as those used in EIA (enzyme immunoassay).

Where X and Y are substances which form a specifically binding pair, fluorescent pigments such as Fluorescein, Rhodamin, Cy5, Cy3, Texas Red and ruthenium complex, electrochemically detectable substances such as ferrocene derivatives, luminescent substances such as lucigenin derivatives and luminol derivatives, or enzymes such as those used in EIA (enzyme immunoassay), can be bound via X and Y.

The electrochemically or photochemically active insertion agent used in the present invention is not particularly limited. Examples thereof include ethidium, ethidium bromide, acridine, aminoacridine, acridine orange, bisbentimide, diamino phenyl indole, proflavin, ellipticine, actinomycin D, thiazol, chromomycin, donomycin, mytomycin C, and derivatives thereof. Further, other examples of insertion agents that can be used include those described in Japanese Laid-Open Patent Publication No. 62-282599.

Further, specific examples of insertion agents which can be used in the present invention are shown below.

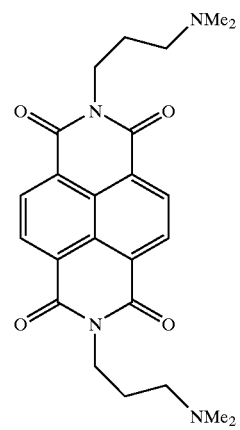

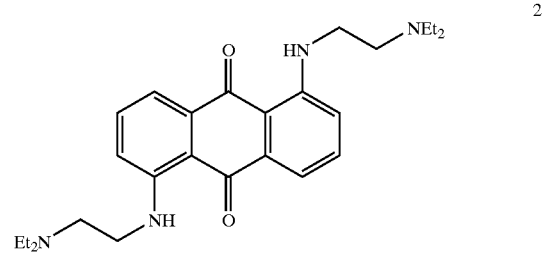

-continued

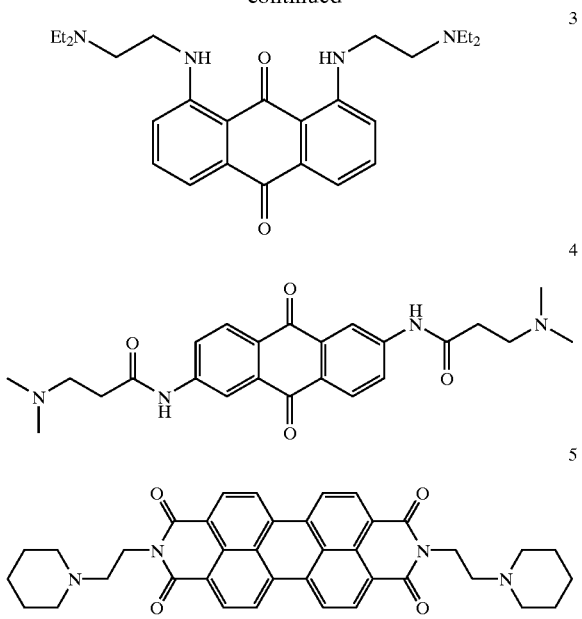

One preferred embodiment of the present invention includes a process of preparing a slide (support) on which a substance which bonds to double stranded DNA is immobilized, and reacting the slide (support) with an analyte.

The present invention will be explained in detail with the use of the following Examples. However, the present invention is not limited to these examples.

EXAMPLES

Example 1

(1) Immobilization of Antibody

1 μl of PBS solution containing double strand recognizing antibody (manufactured by Funakoshi, 1 μg/ml) was spotted onto a slide glass (3DLINK: manufactured by Thermodics) and allowed to stand for 12 hours. Further, this slide glass was immersed in 0.5M Glycine boronate for 30 minutes and then washed with PBS.

(2) Preparation of Samples

The translated region (ORF) of Human alpha 2-HS-glycoprotein (HSGP) was cloned between the NotI and XhoI sites of multicloning sites of pBluescript II SK-. HSGP cDNA was amplified by a PCR method using this vector as a template.

(3) Reaction cDNA amplified by PCR was dissolved in TE to prepare a 0.1 μM solution which was denoted as Sample A. Sample A was boiled at 95° C. for 3 minutes, and then quenched in an ice bath to prepare single stranded Sample B.

10 μl of each of Sample A and Sample B were respectively spotted onto spot portions on antibody immobilized slides prepared in the above (1). After allowing the slides to stand for 1 hour, the slides were washed with TE solution. Further, these slides were immersed in SybrGreen solution (Molecular Probe, 1000-times diluted TE solution) for 20 minutes and then washed with TE.

The washed slide glasses was air-dried, and fluorescence intensity was measured by excitation at 633 nm with FLA2000 (manufactured by Fuji Photo Film Co.). Results are shown below.

|  | Fluorescence intensity |
|---|---|
| Sample A | 14300 LAU |
| Sample B | 6400 LAU |
| Background | 3500 LAU |

(LAU is an unit which is proportional to fluorescence intensity)

The above results show that double stranded DNA can be detected by the method of the present invention.

Example 2

(1) Imobilization of Antibody

1 μl of PBS solution containing double strand recognizing antibody (manufactured by Funakoshi, 1 μg/ml) was spotted onto a gold electrode (2.5 mm φ) arranged on a plate, onto the surface of which a succimide group was introduced via sulfur atom (S), and allowed to stand for 12 hours. Further, this gold electrode surface was immersed in 0.5M Glycine boronate for 30 minutes and then washed with PBS.

(2) Preparation of Sample

The translated region (ORF) of Human alpha 2-HS-glycoprotein (HSGP) was cloned between the NotI and XhoI sites of multicloning sites of pBluescript II SK-. HSGP cDNA was amplified by a PCR method using this vector as a template.

(3) Reaction cDNA amplified by PCR was dissolved in TE to prepare a 0.1 μM solution. This solution was then used as a sample.

10 μl of this sample was spotted on the surface of the gold elect-rode on which double strand recognizing antibody was immobilized as prepared in the above (1). Thereafter, a voltage of 1.5V was applied to the surface of this gold electrode and after allowing to stand for 15 minutes, the electrode was washed with TE solution.

(4) Assay

Further, this gold electrode was immersed in SybrGreen solution (Molecular Probe, 1000-times diluted TE solution) for 20 minutes and then washed with TE. The washed gold electrode was air-dried, and fluorescence intensity was measured by excitation at 633 nm using FLA 2000 (Fuji Photo Film Co.).

Example 3

Fluorescence intensity was measured in a similar manner as in Example 2 except that a voltage of 1.5V is not applied to the surface of the gold electrode in (3) of Example 2. Results of Example 2 and Example 3 are shown below.

|  | Fluorescence intensity |
|---|---|
| Example 2 | 16500 LAU |
| Example 3 | 7500 LAU |
| Background | 3500 LAU |

(LAU is an unit which is proportional to fluorescence intensity)

The results of Example 2 and Example 3 show that double stranded DNA can be detected by the method of the present invention. In particular, Example 2 shows that double stranded DNA can be detected in a promoted reaction by applying an electric field to direct double stranded DNA present in the analyte toward the double stranded DNA recognizing substance immobilized on the support.

Example 4

(1) Immobilization of Antibodies, (2) Preparation of Sample, and (3) Reaction were performed in the same way as in Example 2. Thereafter, the gold electrode (acting electrode), platinum (counter electrode)-and silver/silver chloride reference electrode used in the above operations (1) to (3), were immersed in a mixture of a 0.1M acetic acid-potassium acetate aqueous solution (pH5.6) containing an intercalator (50 mM) having an electrochemical activity which was synthesized by the method described in Japanese Patent Application No. 11-349286 and was represented by the formula below, and a 0.1M potassium chloride aqueous solution, so as to form a tripolar electrode. Then using CV50W (BAS), differential pulse voltammetry measurement (DPV) was performed. From this DPV, a value for peak current at applied voltage 260 mV was determined.

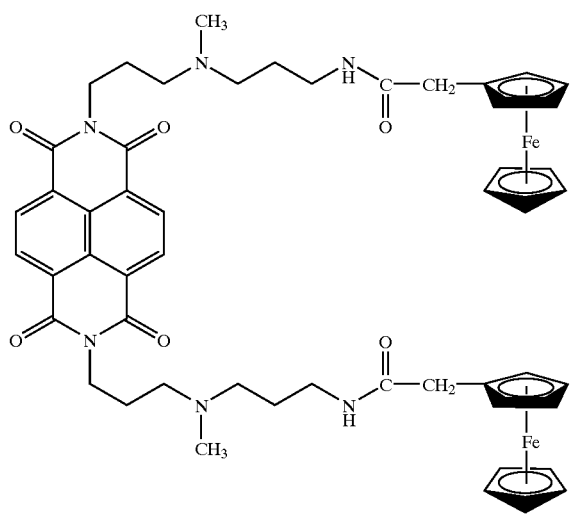

Example 5

DPV measurement was performed in the same way as in Example 4 except that a voltage of 1.5V was not applied to the surface of the gold electrode, and a value for peak current at applied voltage 260 mV was determined. The results of Example 4 and Example 5 are shown below.

|  | Peak current |
| --- | --- |
| Example 4 | −6.8 μA |
| Example 5 | −2.1 μA |
| Background | −0.4 μA |

("background" indicates peak current at the time of DPV measurement at the gold electrode prior to reacting with a sample)

The results of Example 4 and Example 5 show that double stranded DNA can be detected by the method of the present invention. In particular, Example 4 shows that double stranded DNA can be detected in a promoted reaction by applying an electric field to direct double stranded DNA present in the analyte toward the double stranded DNA recognizing substance immobilized on the support.

The present invention enables the analysis of double stranded DNA directly without denaturation. Further, the present invention enables the analysis of double stranded DNA directly without denaturation at a promoted reaction speed. The method of the present invention enables simple, rapid and highly sensitive analysis of double stranded DNA.

The contents of the specifications of Japanese Patent Applications Nos. 2000-325136 and 2000-332249, based on which the present application claims priorities, are hereby incorporated in their entirety into the disclosure of the present specification.

What is claimed is:

1. A method of analyzing a double stranded DNA present in an analyte, which comprises the steps of:

(1) contacting the analyte with a double stranded DNA recognizing substance immobilized on a support, (2) applying an electric field between the support on which the double stranded DNA recognizing substance is immobilized and the analyte, to direct the double stranded DNA present in the analyte toward the double stranded DNA recognizing substance immobilized on the support, (3) applying an electric field in a direction which is opposite to the direction of the electric field applied in step (2), and (4) measuring the double stranded DNA bound to the double stranded DNA recognizing substance, wherein the support and the analyte is within the electric field.

2. The method of analysis according to claim 1 wherein the double stranded DNA recognizing substance is a double stranded DNA recognizing antibody.

3. The method of analysis according to claim 1 wherein the double stranded DNA recognizing substance is a DNA transcription factor.

4. The method of analysis according to claim 1 wherein the double stranded DNA recognizing substance is a protein having Zn finger motif or Ring finger motif.

5. The method of analysis according to claim 1 wherein the double stranded DNA recognizing substance is a peptide nucleic acid.

6. The method of analysis according to claim 1 wherein, in the step of measuring the double stranded DNA bound to the double stranded DNA recognizing substance, an insertion agent which recognizes double stranded DNA is added to a reaction system, and the double stranded DNA present in the analyte is measured by detecting the insertion agent inserted into the double stranded DNA.

7. The method of analysis according to claim 6 wherein the insertion agent is a DNA intercalator.

8. The method of analysis according to claim 7 wherein the DNA intercalator has an electrochemical activity, and the double stranded DNA present in the analyte is measured by detecting the DNA intercalator by electrochemical means.

9. The method of analysis according to claim 7 wherein the DNA intercalator is detected by a fluorescence, luminescence or surface plasmon method.

* * * * *